United States Patent [19]
Abe et al.

[11] Patent Number: 5,322,612
[45] Date of Patent: Jun. 21, 1994

[54] CARBON DIOXIDE GAS DETECTION ELEMENT

[75] Inventors: Tooru Abe; Takaaki Kuroiwa; Yoshihiko Sadaoka, all of Kanagawa, Japan

[73] Assignee: Yamatake-Honeywell Co., Ltd., Tokyo, Japan

[21] Appl. No.: 930,148

[22] Filed: Aug. 13, 1992

[30] Foreign Application Priority Data

Aug. 14, 1991 [JP] Japan .................. 3-228597

[51] Int. Cl.$^5$ .............................................. G01N 27/26
[52] U.S. Cl. .................................... 204/421; 204/416; 204/419; 204/424; 204/426; 501/32; 501/153

[58] Field of Search .............. 204/419, 421, 424, 425, 204/426, 427, 428, 429, 153.18, 153.12, 416; 501/153, 32

[56] References Cited

U.S. PATENT DOCUMENTS

| | | |
|---|---|---|
| 4,388,155 | 6/1983 | Chamberland et al. ............ 204/426 |
| 4,855,034 | 8/1989 | Sugimoto et al. .................... 204/424 |
| 5,047,374 | 9/1991 | Nicholson et al. ................... 501/32 |
| 5,120,422 | 6/1992 | Liu et al. ............................. 204/421 |

*Primary Examiner*—John Niebling
*Assistant Examiner*—Bruce F. Bell
*Attorney, Agent, or Firm*—Blakely, Sokoloff, Taylor & Zafman

[57] ABSTRACT

A carbon dioxide gas detection element includes a solid electrolyte of a sodium ion conductor made of a ceramic/glass composite material.

3 Claims, 8 Drawing Sheets

CARBON DIOXIDE GAS DETECTION ELEMENT

BACKGROUND OF THE INVENTION

The present invention relates to a carbon dioxide gas detection element.

As a carbon dioxide gas detection element, a solid-electrolyte type carbon dioxide gas detection element has been used. A sodium ion conductor has been used as a solid electrolyte.

Since a conventional sodium ion conductor is formed by sintering a ceramic material as a crystal powder, through holes are sometimes formed in the conductor. If through holes are formed in the ion conductor, the electromotive force generated by the difference in carbon dioxide gas concentration between a detection pole and a reference pole cannot be stabilized. In addition, the residual carbon dioxide gas in cavities increases the hysteresis. Furthermore, a deterioration in repeating reproducibility occurs.

SUMMARY OF THE INVENTION

It is a principal object of the present invention to provide a carbon dioxide gas detection element which has excellent repeating reproducibility as well as good response characteristics.

In order to achieve the above object, a carbon dioxide gas detection element of the present invention uses a solid electrolyte of a sodium ion conductor made of a ceramic/glass composite material. With the use of the ceramic/glass composite material, the denseness of the solid electrolyte can be increased, thus providing a carbon dioxide gas detection element which is excellent in response characteristics and repeating reproducibility.

DESCRIPTION OF THE PREFERRED EMBODIMENT

An embodiment of the present invention will be described in detail below with reference to the accompanying drawings.

Figure 1:
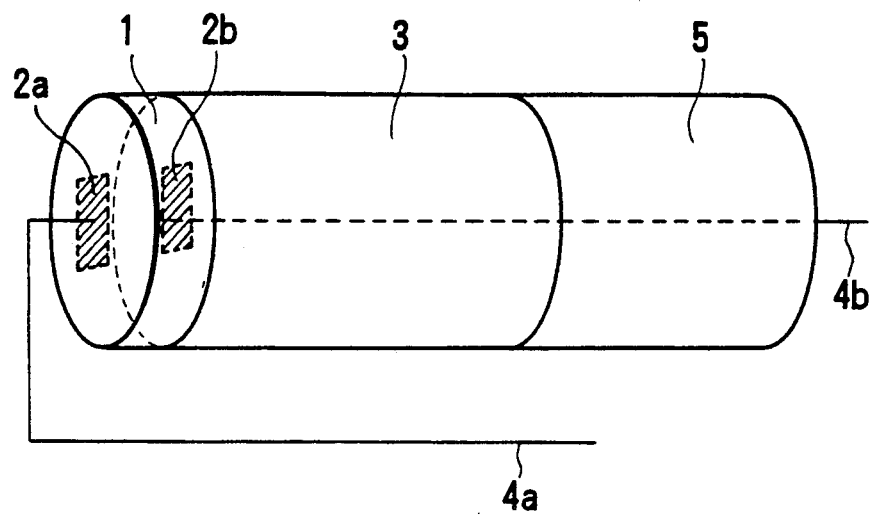
FIG. 1 is a perspective view showing a detecting portion of a carbon dioxide gas detection element according to an embodiment of the present invention.

FIG. 1 shows the arrangement of a detecting portion of a carbon dioxide gas detection element according to an embodiment of the present invention. Referring to FIG. 1, reference number 1 denotes a solid electrolyte of a sodium ion conductor made of a ceramic/glass composite material; 2$a$, a porous platinum electrode at the detection pole side; 2$b$, a platinum electrode at the reference pole side; 3, an alumina pipe which is bonded and sealed to a pellet-like solid electrolyte 1 and is welded to a glass pipe 5 arranged on the rear side of the alumina pipe 3; 4$a$, a platinum lead electrically connected to the platinum electrode 2$a$ at the detection pole side; and 4$b$, a platinum lead connected to the platinum electrode 2$b$ at the reference pole side.

Figure 2:
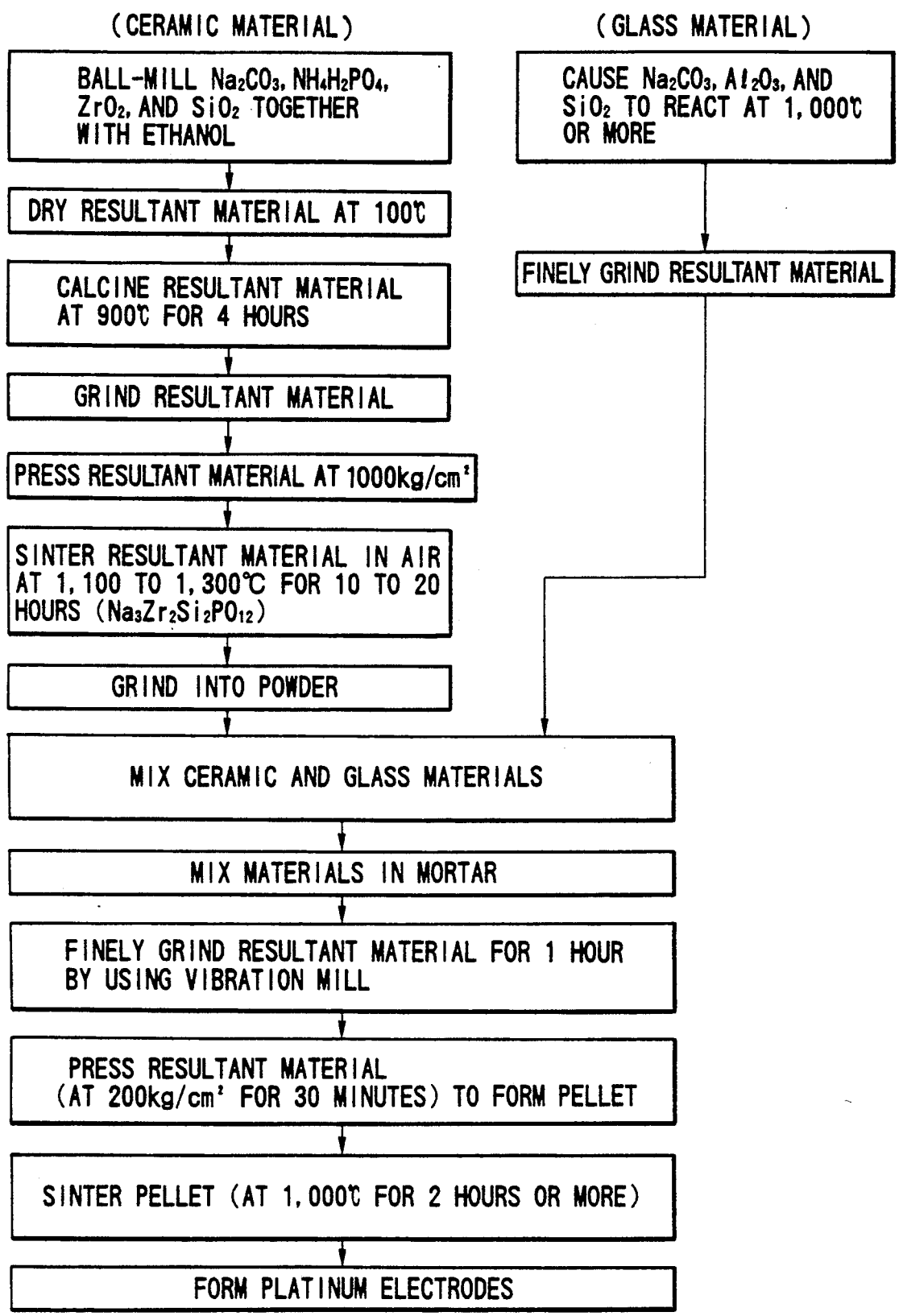
FIG. 2 is a flow chart for explaining the steps in manufacturing a carbon dioxide gas detection element according to the present invention.

A method of manufacturing the carbon dioxide gas detection element of the present invention will be described below with reference to FIG. 2.

A crystal powder as a ceramic material was prepared as follows. Reagent class $NaCO_3$, $NH_4H_2PO_4$, $ArO_2$, , and $SiO_2$ were ball-milled together with ethanol. The resultant material was dried at 100° C., calcined in the air at 900° C. for 4 hours, and ground. The crystal powder was then pressed at 1,000 kg/cm$^2$ to be formed into a pellet. The pellet was sintered in the air at 1,100° to 1,300° C. for 10 to 20 hours to obtain a crystalline ceramic material ($Na_3Zr_2Si_2PO_{12}$). Thereafter, the ceramic material was ground into a powder.

A glass material was prepared as follows. Reagent class $Na_2CO_3$, $Al_2O_3$ and $SiO_2$ were caused to react at 1,000° C. or more to obtain a glass material $Na_2O\text{-}Al_2O_3\text{-}4SiO_2$. Thereafter, the glass material was ground into a powder.

The glass material was mixed with the ceramic material in amounts of 10, 20, 30, 40, and 50 wt% by using a mortar. The mixtures were finely ground by a vibration mill for 1 hour. Each ground material was pressed at 200 kg/cm$^2$ for 30 minutes to obtain a pellet (thickness: 1.5 mm; diameter: 1 cm). This pellet was sintered at 1,000° C. for 2 hours or more to obtain a solid electrolyte of a sodium ion conductor made of a ceramic/glass composite material. Platinum pastes (4×4 mm) were respectively coated on the upper and lower surfaces of the pellet and were baked to form platinum electrodes, thereby manufacturing a sandwich type carbon dioxide gas detection element.

A device for measuring the characteristics of the actually manufactured carbon dioxide gas detection elements will be described next.

Each of the sandwich type carbon dioxide gas detection elements was left to stand in a dryer (at 60° C.) for 24 hours to be bonded to an alumina pipe (outer diameter: 1 cm; inner diameter: 0.6 cm; length: 10 cm) by using a glass material containing sodium. The alumina pipe was then welded to a glass pipe (outer diameter 1 cm; inner diameter: 0.6 cm; length: 15 cm). In addition, a droplet of a saturated sodium carbonate solution was applied to the platinum electrode at the detection pole side of the carbon dioxide gas element.

Figure 3:
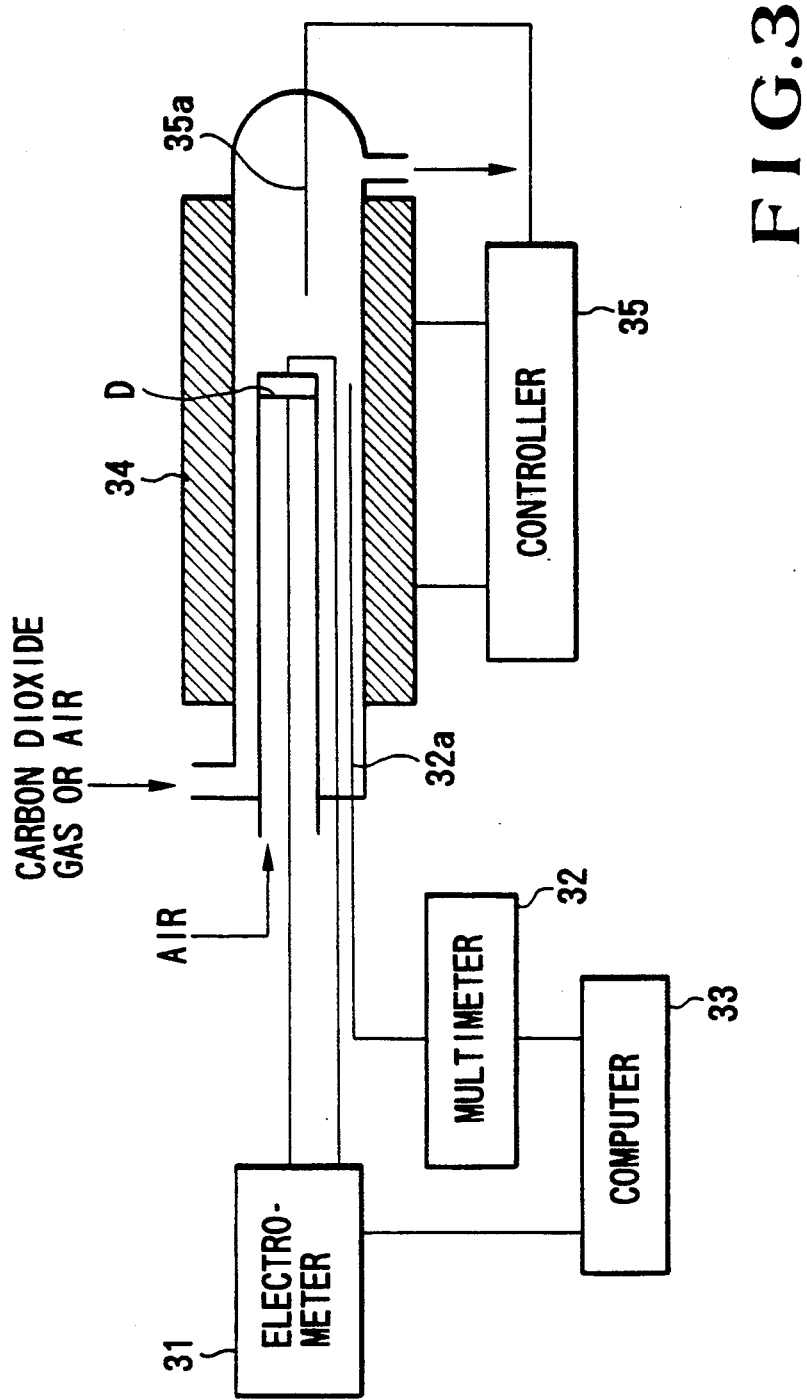
FIG. 3 is a block diagram showing a measuring device for measuring the characteristics of the carbon dioxide gas detection element of the present invention.

Each of the carbon dioxide gas detection elements manufactured in the above-described manner was placed in the measuring device shown in FIG. 3. In measurement, the electromotive force of a carbon dioxide gas detection element D was measured by an electrometer 31, and the ambient temperature was measured by a multimeter 32 by using a thermocouple 32$a$. The measured values were supplied to a computer 33. The ambient temperature in an infrared furnace 34 was controlled by a temperature controller 35 using a thermocouple 35$a$. Synthetic air (flow rate: 100 ml/min) was caused to flow at the reference pole side, while synthetic air (flow rate: 100 ml/min) and a 999-ppm carbon dioxide gas (flow rate: 100 ml/min) were alternately caused to flow for 20 minutes and for 10 minutes, respectively, thus performing measurement. Note that the ambient temperature was set to be 470° C.

The measurement results obtained by the above-described measuring device will be described below.

Figure 4:
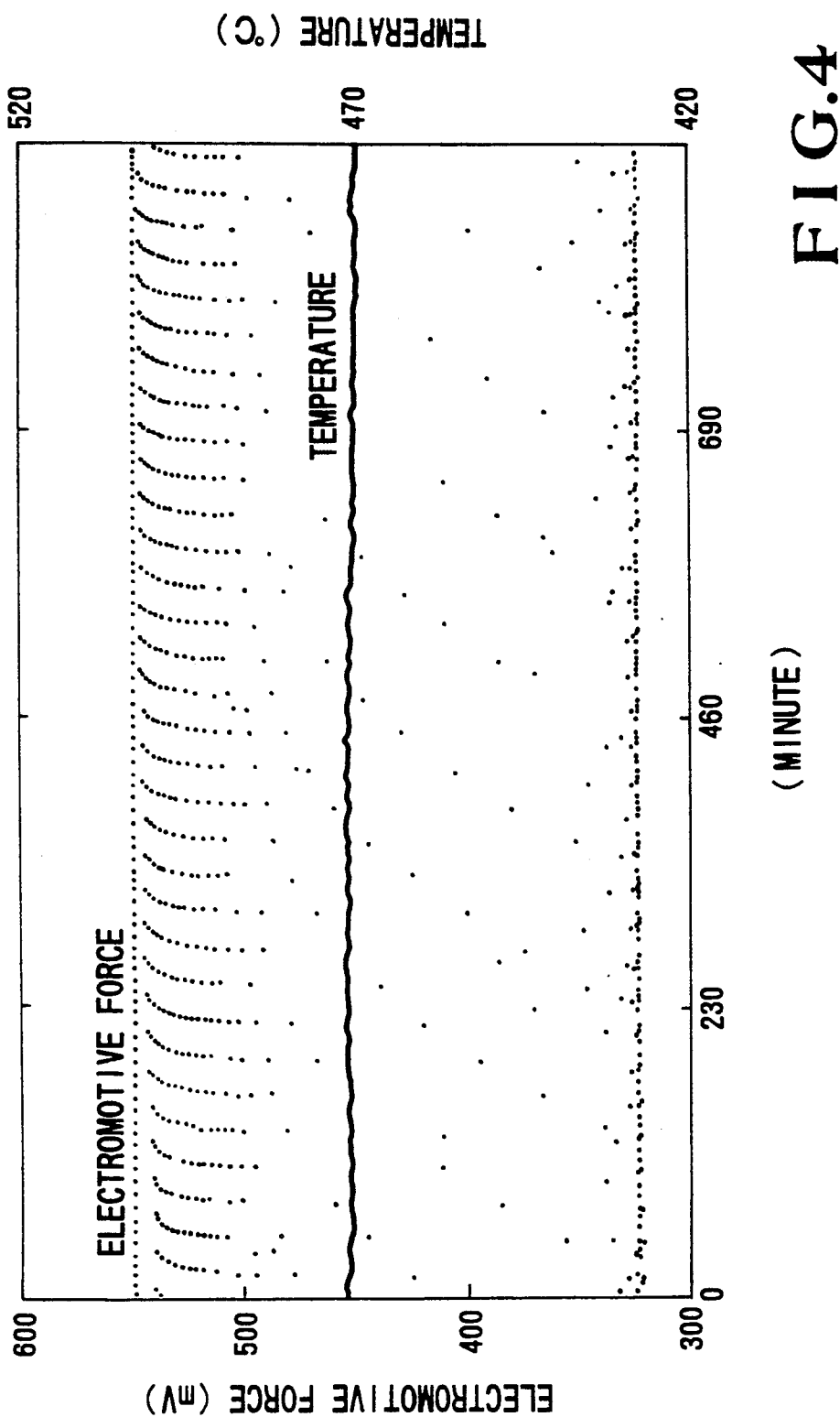
FIG. 4 is a view showing the characteristics of a ceramic/glass composite material.

FIG. 4 shows the characteristics of the solid electrolyte of the ceramic/glass composite material in which the glass material is mixed at 20 wt%. Even after the repeating response of the solid electrolyte is measured 30 times or more, the characteristics are stable, and hence a carbon dioxide gas detection element having excellent repeating reproducibility is realized. In addition, according to FIG. 4, a 90% response is obtained in 60 seconds or less (a 90% response is obtained at one point at measurement intervals of 20 to 60 seconds).

Figure 5:
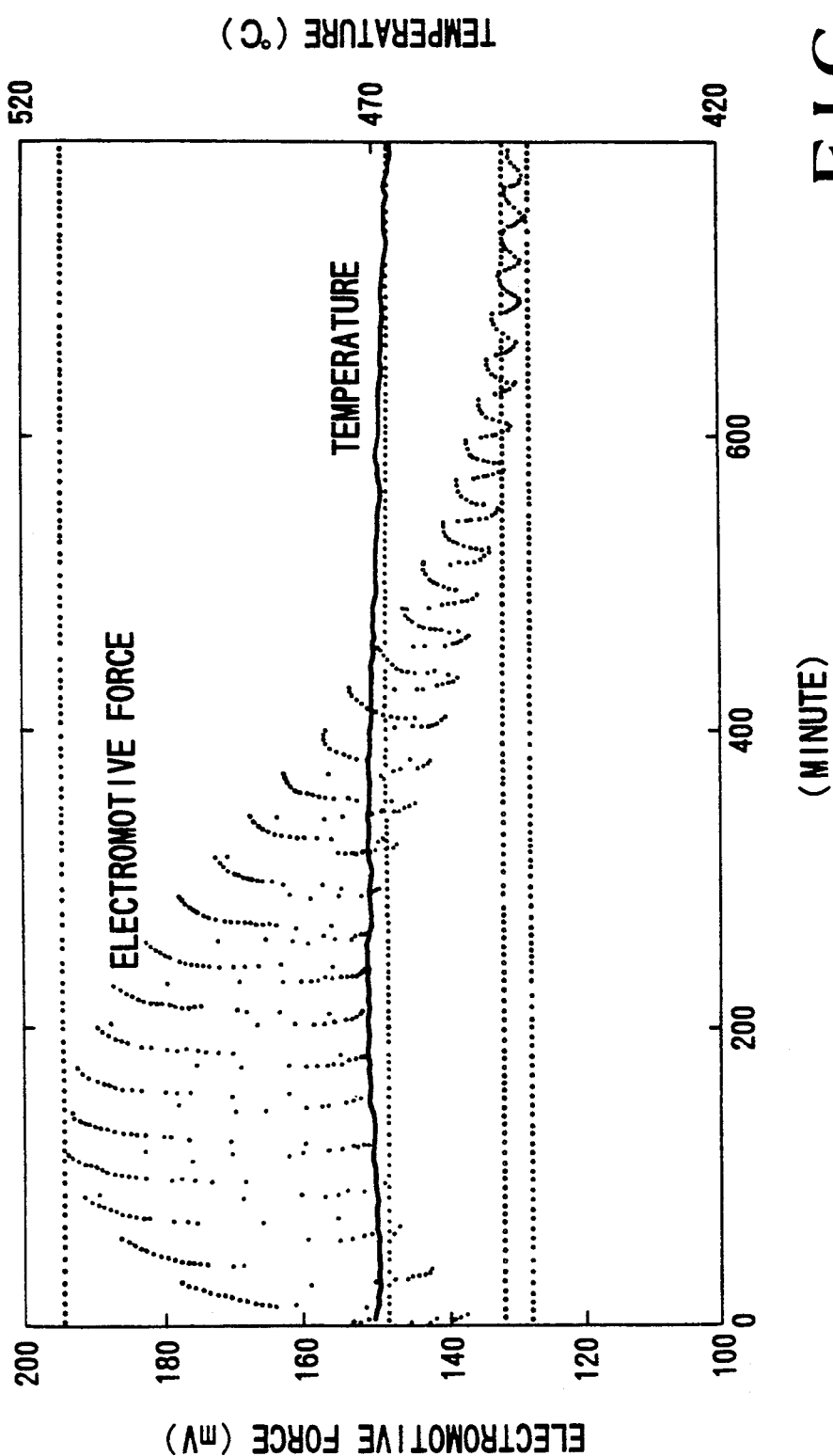
FIG. 5 is a view showing the characteristics of a ceramic material.

FIG. 5 shows the characteristics of a conventional carbon dioxide gas detection element, as a comparative example, constituted by a solid electrolyte of a sodium ion conductor made of only a ceramic material (crystalline) without a glass material. Although an electromotive force is initially generated, its characteristic is not stable. In addition, the repeating reproducibility of the conventional element is much inferior to that of the ceramic/glass composite material shown in FIG. 5.

Figure 6:
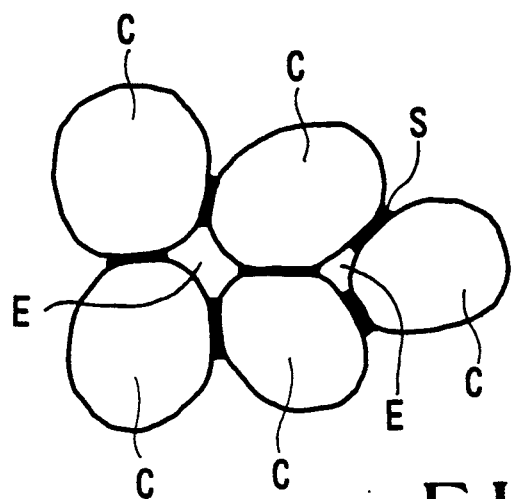
FIG. 6 is a view showing a sintered ceramic material.
Figure 7:
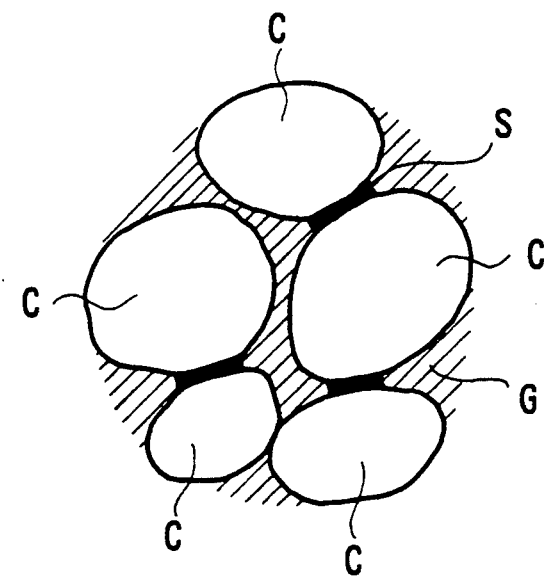
FIG. 7 is a view showing a sintered ceramic/glass composite material.

As described above, the difference in characteristics between a ceramic material and a ceramic/glass composite material is based on their sintered structures. As shown in FIG. 6, in the sintered structure of the ceramic material, cavities E are easily formed between ceramic crystal grains C. Note that a reference symbol S denotes a contact portion. In contrast to this, in the ceramic/glass composite material, as shown in FIG. 7, since a glass G having ion conductivity exists like a paste between ceramic crystal grains C, the cavities E shown in FIG. 6 are not easily formed. Even if cavities are formed in the ceramic/glass composite material, no cavity (through hole) extending through the sintered element is produced.

Figure 8A:
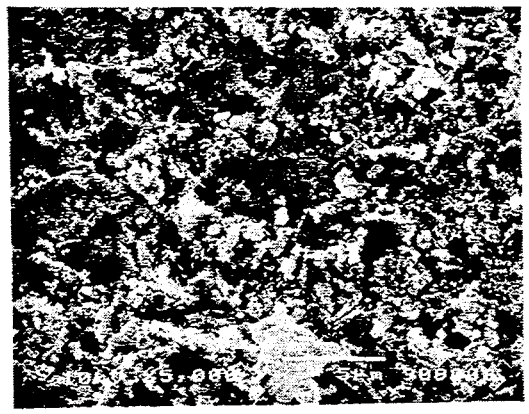
FIGS. 8($a$) and 8($b$) are views showing a sintered ceramic material.
Figure 8B:
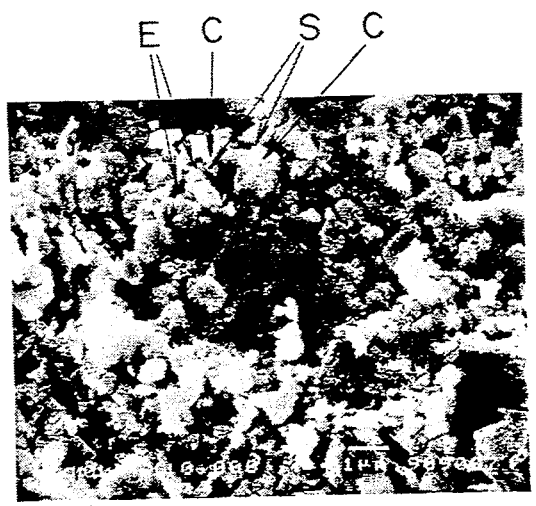
Figure 9A:
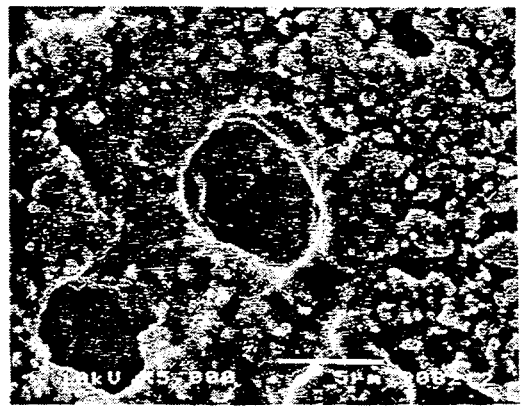
FIGS. 9($a$) and 9($b$) are views showing a sintered ceramic/glass composite material.
Figure 9B:
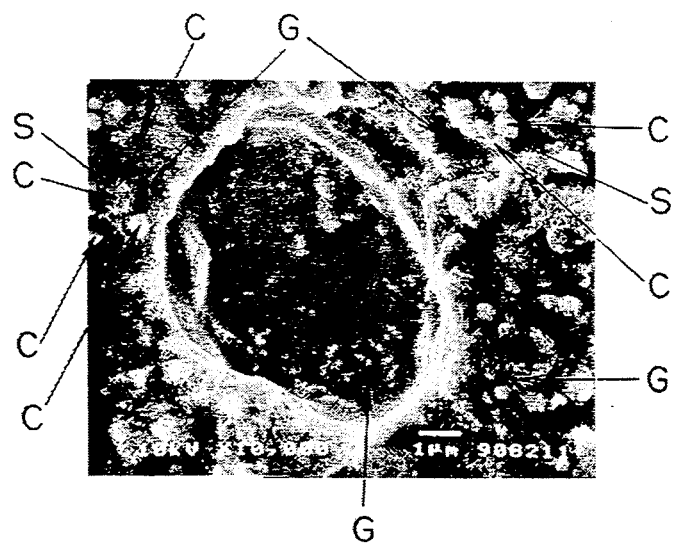

FIGS. 8(a) to 9(b) are photographs showing the sectional structures of actual ceramic and ceramic/glass composite materials. FIGS. 8(a) and 8(b) show the sectional structure of the element formed by sintering a ceramic material. FIG. 8(a) shows the sectional structure at a magnification of ×5,000. FIG. 8(b) shows the sectional structure at a magnification of ×10,000. According to these photographs, a large number of minute cavities exist around ceramic crystal grains, and these cavities are assumed to communicate with each other. In contrast to this, according to the sintered structure of the ceramic/glass composite material (weight ratio of glass material: 20 wt%) shown in FIGS. 9(a) and 9(b), as shown in FIG. 9(a) at a magnification of ×5,000 and in FIG. 9(b) at a magnification of ×10,000, a dense sectional structure is obtained. Even if, therefore, cavities are formed in the sintered structure, no cavity (through hole) extending through the element is present.

As described above, since a carbon dioxide gas detection element is made of a ceramic/glass composite material, a dense structure is achieved, thereby realizing a carbon dioxide gas detection element which is excellent in response characteristics and repeating reproducibility. As indicated in this embodiment, the glass material used for the composite material is a glass material having sodium ions as the same carrier ions as those of the ceramic material.

In the above-described embodiment, the amount of a glass material to be mixed is set to be 20 w%. However, the present invention is not limited to this. As long as the weight ratio of the glass material is 50 wt% or less, the element characteristics can be improved as compared with the element constituted by only a ceramic material. However, at less than 10 wt%, the conductivity has an inflection point, and hence a stable conductivity cannot be obtained. Note that if the weight ratio of the glass material exceeds 50 wt%, the conductivity is decreased, and the element is deformed in the sintering process, resulting in difficulty in forming the element into a predetermined shape.

As has been described above, according to the present invention, since an improvement in denseness of a solid electrolyte can be achieved because of the use of a ceramic/glass composite material, a carbon dioxide gas detection element which is excellent in response characteristics and repeating reproducibility can be realized.

What is claimed is:

1. A carbon dioxide gas detection element comprising a solid electrolyte of a sodium ion conductor made of a composite material of a ceramic and glass materials, said glass material comprising $Na_2O\text{-}Al_2O_3\text{-}4SiO_2$.

2. An element according to claim 1, wherein the glass material has the same carrier ions as those of the ceramic material.

3. An element according to claim 1, wherein a weight ratio of the glass material with respect to the ceramic material is set to be not more than 50 wt%.

* * * * *

UNITED STATES PATENT AND TRADEMARK OFFICE
CERTIFICATE OF CORRECTION

PATENT NO. : 5,322,612
DATED : June 21, 1994
INVENTOR(S) : Abe et al.

It is certified that error appears in the above-indentified patent and that said Letters Patent is hereby corrected as shown below:

In column 2 at line 14 delete "$NaCo_3$, $NH_4H_2PO_4$, $ArO_2$, ," and insert --$NaCo_3$, $NH_4H_2PO_4$, $ZrO_2$,--

In column 3 at line 10 delete "30times" and insert --30 times--.

Signed and Sealed this

Twenty-fourth Day of October, 1995

Attest:

BRUCE LEHMAN

Attesting Officer

Commissioner of Patents and Trademarks